(12) United States Patent
Zimmerling

(10) Patent No.: US 12,064,626 B2
(45) Date of Patent: *Aug. 20, 2024

(54) FIXATION OF A REMOVABLE MAGNET OR A SIMILAR ELEMENT IN AN ELASTIC IMPLANT MATERIAL

(71) Applicant: MED-EL Elektromedizinische Geraete GmbH, Innsbruck (AT)

(72) Inventor: Martin Zimmerling, Patsch (AT)

(73) Assignee: MED-EL Elektromedizinische Geraete, Innsbruck (AT)

( * ) Notice: Subject to any disclaimer, the term of this patent is extended or adjusted under 35 U.S.C. 154(b) by 729 days.

This patent is subject to a terminal disclaimer.

(21) Appl. No.: 17/102,071

(22) Filed: Nov. 23, 2020

(65) Prior Publication Data

US 2021/0077813 A1 Mar. 18, 2021

Related U.S. Application Data

(63) Continuation of application No. 15/452,819, filed on Mar. 8, 2017, now Pat. No. 10,842,994, which is a
(Continued)

(51) Int. Cl.
*A61N 1/37* (2006.01)
*A61N 1/05* (2006.01)
(Continued)

(52) U.S. Cl.
CPC ........... *A61N 1/36038* (2017.08); *A61N 1/05* (2013.01); *A61N 1/0541* (2013.01);
(Continued)

(58) Field of Classification Search
CPC ............... H04R 25/60–65; H04R 2225/67
See application file for complete search history.

(56) References Cited

U.S. PATENT DOCUMENTS

| | | | |
|---|---|---|---|
| 4,606,329 A * | 8/1986 | Hough | H04R 25/606 381/326 |
| 5,927,277 A | 7/1999 | Baudino et al. | |

(Continued)

FOREIGN PATENT DOCUMENTS

WO WO 2017/044523 A1 3/2017

OTHER PUBLICATIONS

International Searching Authority/US, International Search Report and Written Opinion of the International Searching Authority, Application No. PCT/US2016/50619, dated Nov. 29, 2016 17 pages.
(Continued)

*Primary Examiner* — Eric D. Bertram
(74) *Attorney, Agent, or Firm* — BURNS & LEVINSON LLP

(57) ABSTRACT

A magnet arrangement for an implantable medical device is described. An implantable coil case contains a communications coil and is made of biocompatible resilient material with a top lateral surface. A magnet receptacle is located within the coil case and has a receptacle opening in the top lateral surface. An implant magnet fits within the magnet receptacle and has opposing end surfaces, and a center body region located between the end surfaces. An elastic opening clamp is located radially around the receptacle opening and is configured to normally be closed around the receptacle opening to maintain the implant magnet within the magnet receptacle. The elastic opening clamp also is configured to cooperate with a surgical handling tool to expand the receptacle opening to permit the implant magnet to be removed from the magnet receptacle through the receptacle opening without needing to move the coil case.

20 Claims, 9 Drawing Sheets

Related U.S. Application Data continuation-in-part of application No. PCT/US2016/050619, filed on Sep. 8, 2016.

(60) Provisional application No. 62/215,805, filed on Sep. 9, 2015.

(51) Int. Cl.
 *A61N 1/36* (2006.01)
 *A61N 1/372* (2006.01)
 *A61N 1/375* (2006.01)
 *H04R 25/00* (2006.01)

(52) U.S. Cl.
 CPC ...... *A61N 1/36036* (2017.08); *A61N 1/37211* (2013.01); *A61N 1/37223* (2013.01); *A61N 1/3758* (2013.01); *H04R 25/606* (2013.01); *H04R 2225/67* (2013.01)

(56) References Cited

U.S. PATENT DOCUMENTS

| | | | |
|---|---|---|---|
| 6,178,353 B1* | 1/2001 | Griffith | A61N 1/37276 607/61 |
| 6,387,096 B1 | 5/2002 | Hyde, Jr. | |
| 8,340,774 B2 | 12/2012 | Hochmair et al. | |
| 8,768,480 B2 | 7/2014 | Charvin | |
| 8,825,171 B1 | 9/2014 | Thenuwara et al. | |
| 9,352,149 B2 | 5/2016 | Thenuwara et al. | |
| 9,393,428 B2* | 7/2016 | Nyberg, II | A61N 1/37229 |
| 10,758,736 B2* | 9/2020 | Zimmerling | A61N 1/37211 |
| 10,806,936 B2* | 10/2020 | Crawford | A61N 1/3758 |
| 10,842,994 B2* | 11/2020 | Zimmerling | A61N 1/05 |
| 2008/0009920 A1* | 1/2008 | Gibson | A61N 1/3787 607/57 |
| 2008/0221641 A1 | 9/2008 | Hochmair et al. | |
| 2009/0099403 A1* | 4/2009 | Zimmerling | A61F 11/04 600/12 |
| 2009/0287278 A1* | 11/2009 | Charvin | A61N 1/36038 607/57 |
| 2009/0299437 A1 | 12/2009 | Zimmerling | |
| 2011/0264172 A1 | 10/2011 | Zimmerling et al. | |
| 2012/0296155 A1 | 11/2012 | Ball | |
| 2013/0018218 A1 | 1/2013 | Haller et al. | |
| 2014/0343626 A1* | 11/2014 | Thenuwara | B29C 45/14819 607/57 |
| 2015/0025613 A1* | 1/2015 | Nyberg, II | A61N 1/37229 29/601 |
| 2015/0087892 A1 | 3/2015 | Tourrel et al. | |
| 2016/0037273 A1* | 2/2016 | Gustafsson | H04R 25/606 381/326 |
| 2016/0361537 A1* | 12/2016 | Leigh | A61N 1/36038 |
| 2017/0173334 A1* | 6/2017 | Zimmerling | A61N 1/05 |
| 2018/0110986 A1* | 4/2018 | Lee | A61N 1/36038 |
| 2018/0243571 A1* | 8/2018 | Zimmerling | A61N 1/05 |
| 2018/0304078 A1* | 10/2018 | Crawford | A61N 1/37217 |

OTHER PUBLICATIONS

International Searching Authority/US, International Search Report and Written Opinion of the International Searching Authority, Application No. PCT/US2018/021255, dated May 23, 2018, 11 pages.

* cited by examiner

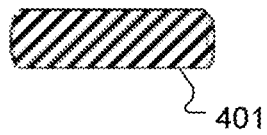
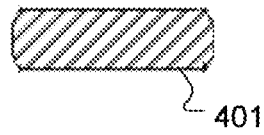
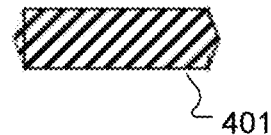
*Fig. 5A*      *Fig. 5B*      *Fig. 5C*
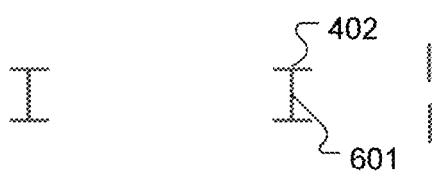
*Fig. 6A*      *Fig. 6B*      *Fig. 6C*
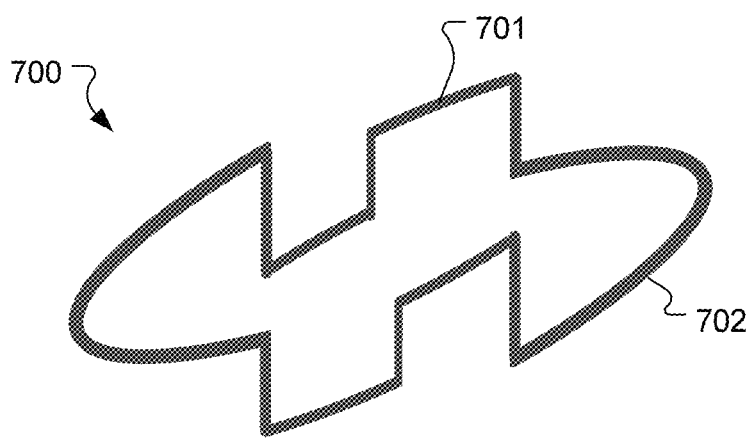
*Fig. 7*

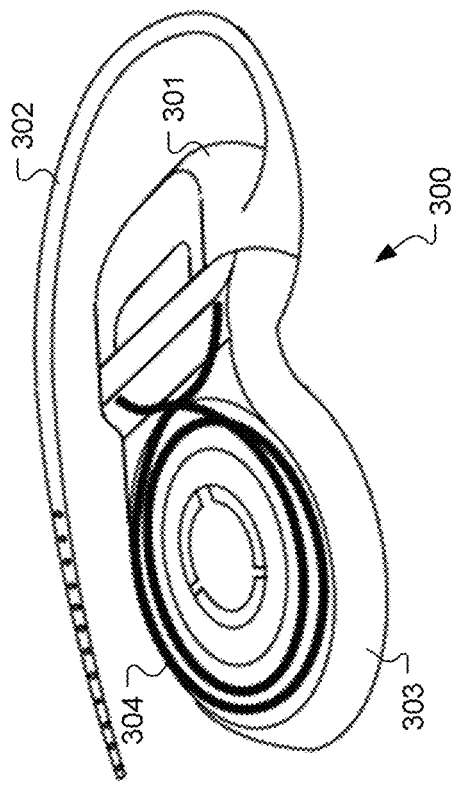
Fig. 12
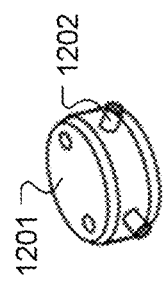
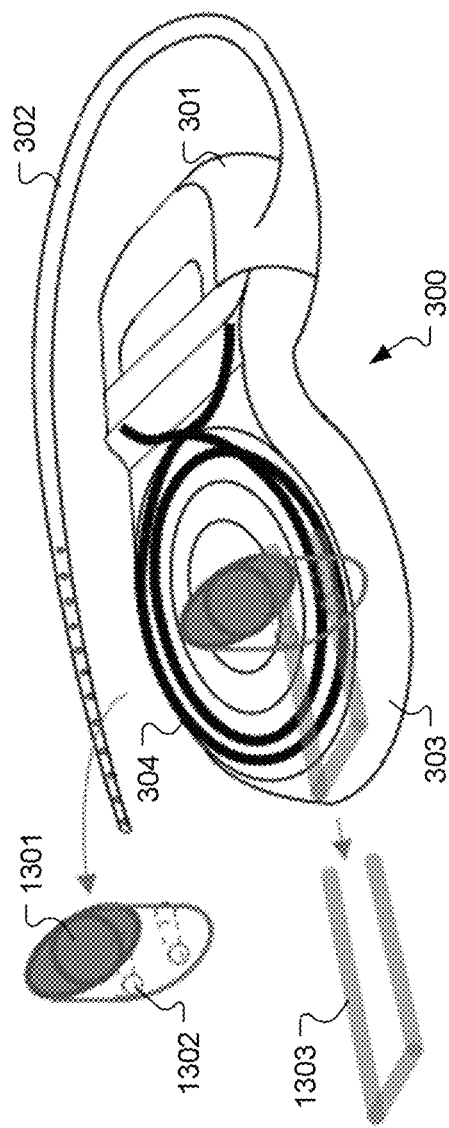
Fig. 13

FIXATION OF A REMOVABLE MAGNET OR A SIMILAR ELEMENT IN AN ELASTIC IMPLANT MATERIAL

This application is a continuation of U.S. patent application Ser. No. 15/452,819 filed Mar. 8, 2017, now U.S. Pat. No. 10,842,994, which is a continuation-in-part of International Patent Application No. PCT/US2016/050619 filed Sep. 8, 2016, which claims priority to U.S. Provisional Patent Application No. 62/215,805, filed Sep. 9, 2015, the disclosures of which are incorporated herein by reference in their entireties.

FIELD OF THE INVENTION

The present invention relates to implantable medical devices, and specifically, to removable magnetic elements in such devices.

BACKGROUND ART

Some hearing implants such as Middle Ear Implants (MEI's) and Cochlear Implants (CI's) employ cooperating attachment magnets located in the implant and the external part to magnetically hold the external part in place over the implant. For example, as shown in FIG. 1, a typical cochlear implant system may include an external transmitter housing 101 containing transmitting coils 102 and an external attachment magnet 103. The external attachment magnet 103 has a conventional cylindrical disc-shape and a north-south magnetic dipole having an axis that is perpendicular to the skin of the patient to produce external magnetic field lines 104 as shown. Implanted under the patient's skin is a corresponding receiver assembly 105 having similar receiving coils 106 and an implant magnet 107. The implant magnet 107 also has a cylindrical disc-shape and a north-south magnetic dipole having a magnetic axis that is perpendicular to the skin of the patient to produce internal magnetic field lines 108 as shown. The internal receiver housing 105 is surgically implanted and fixed in place within the patient's body. The external transmitter housing 101 is placed in proper position over the skin covering the internal receiver assembly 105 and held in place by interaction between the internal magnetic field lines 108 and the external magnetic field lines 104. Rf signals from the transmitter coils 102 couple data and/or power to the receiving coil 106 which is in communication with an implanted processor module (not shown).

One problem arises when the patient undergoes Magnetic Resonance Imaging (MRI) examination. Interactions occur between the implant magnet and the applied external magnetic field for the MRI. As shown in FIG. 2, the direction magnetization m of the implant magnet 202 is essentially perpendicular to the skin of the patient. In this example, the strong static magnetic field $\overline{B}$ from the MRI creates a torque $\overline{T}$ on the internal magnet 202, which may displace the internal magnet 202 or the whole implant housing 201 out of proper position. Among other things, this may damage the adjacent tissue in the patient. In addition, the external magnetic field $\overline{B}$ from the MRI may reduce or remove the magnetization $\overline{m}$ of the implant magnet 202 so that it may no longer be strong enough to hold the external transmitter housing in proper position. The implant magnet 202 may also cause imaging artifacts in the MRI image, there may be induced voltages in the receiving coil, and hearing artifacts due to the interaction of the external magnetic field $\overline{B}$ of the MRI with the implanted device. Torque and forces acting on the implant magnet and demagnetization of the implant magnet are especially an issue with MRI field strengths exceeding 1.5 Tesla.

Thus, for existing implant systems with magnet arrangements, it is common to either not permit MRI or at most limit use of MRI to lower field strengths. Other existing solutions include use of a surgically removable magnets, spherical implant magnets (e.g. U.S. Pat. No. 7,566,296), and various ring magnet designs (e.g., U.S. Provisional Patent 61/227,632, filed Jul. 22, 2009). U.S. Patent Publication 20110264172 describes an implant magnet having a magnetic dipole with a magnetic axis that is parallel to the end surfaces of a disc shaped implant magnet—that is, perpendicular to the conventional magnetic axis of a disc-shaped implant magnet. The magnet is then held in a magnet receptacle that allows the magnet to rotate in response to an external magnetic field such as from an MRI.

Some devices also add a stiffening ring around the magnet to resist torques and help hold the magnet in place. FIG. 3 shows an example of a cochlear implant device 300 with an implantable stimulator 301 that provides electrical stimulation signals to an electrode lead 302 that is implanted in the patient's cochlea. A coil case 303 is made of biocompatible resilient material such as molded silicone in which is embedded a communications coil 304 for transcutaneous communication of an implant communication signal. In the center of coil case 303 is an implant magnet 306 that cooperates with another external holding magnet (not shown) to hold an external coil on the skin of the patient over the implanted communications coil 304. Also embedded in the resilient material of the coil case 303 between the communications coil 304 and the implant magnet 306 is a stiffening ring 305 made of stiffer material than the coil case 303. The stiffening ring 305 is configured to resist mechanical torque movement of the coil case 303 and to promote securement of the implant magnet 306 within the coil case 303. This includes securement of the implant magnet 306 against movement and tilting, and in the case of a removable implant magnet 306, additionally against magnet displacement in lateral direction (i.e. perpendicular to the skin surface).

SUMMARY OF THE INVENTION

Embodiments of the present invention are directed to a magnet arrangement for a hearing implant device. An implantable coil case contains a communications coil and is made of biocompatible resilient material with a top lateral surface. A magnet receptacle is located within the coil case and has a receptacle opening in the top lateral surface. An implant magnet fits within the magnet receptacle and has opposing end surfaces, and a center body region located between the end surfaces. The center body diameter is larger than the end diameters. The magnet receptacle has corresponding enclosing surfaces configured to fit against the different diameter surfaces of the implant magnet to secure the implant magnet within the magnet receptacle. An elastic opening clamp is located radially around the receptacle opening and is configured to normally be closed around the receptacle opening to maintain the implant magnet within the magnet receptacle. The elastic opening clamp also is configured to cooperate with a surgical handling tool to expand the receptacle opening to permit the implant magnet to be removed from the magnet receptacle through the receptacle opening without needing to move the coil case.

In further specific embodiments, the elastic opening clamp may be a c-shaped spring ring element or a c-shaped retainer ring element. The implant magnet may have a magnetic field direction that is parallel to the end surfaces or perpendicular to the end surfaces. The implant magnet and the magnet receptacle may be configured to allow the implant magnet to rotate within the magnet receptacle, or to prevent the implant magnet from rotating within the magnet receptacle.

BRIEF DESCRIPTION OF THE DRAWINGS

FIG. 5 A-C shows cross-sectional views of various different example profiles for an implant magnet according to an embodiment of the present invention.

FIG. 6 A-C shows cross-sectional views of various different example profiles for stiffening ring arrangements according to an embodiment of the present invention.

FIG. 7 shows an example of a bilevel stiffening ring cage according to one embodiment of the present invention.

FIG. 12 shows an elevated perspective view of an implant magnet with bayonet elements according to an embodiment of the present invention.

FIG. 13 shows an elevated perspective view of an implant magnet with a locking pin according to an embodiment of the present invention.

DETAILED DESCRIPTION OF SPECIFIC EMBODIMENTS

In existing implantable medical devices which use removable implant magnets, such as cochlear implants, the implant magnet can be removed and reinserted in only one direction—i.e., either from the medial side of the coil case (underneath), or from the lateral side of the coil case (the top). And in the designs with securement the magnet itself must be properly oriented in a single direction with the correct side up. Embodiments of the present invention have an implant magnet and its elastic magnet receptacle with a symmetrical cross-section that allows the implant magnet to be removed and reinserted in both directions—from underneath on the medial side and from on top from the lateral direction. In addition, specific embodiments also can allow the implant magnet to be inserted into the coil case regardless of the orientation of the disc-shaped magnet, with either end up. The disc-shaped magnet may be without limitation for example cylindrical, elliptical or rectangular with rounded corners.

Figure 1:
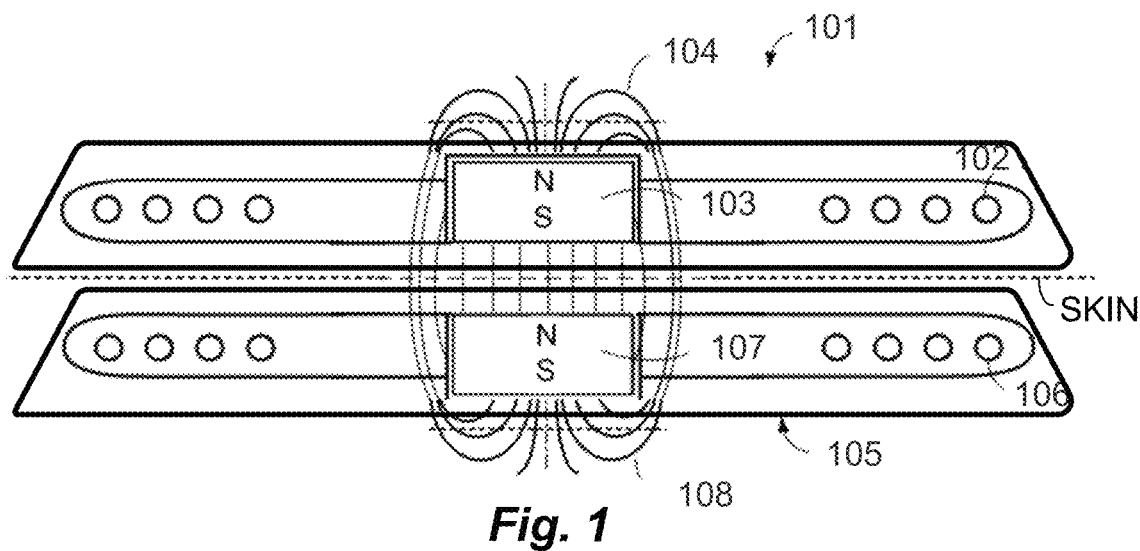
FIG. 1 shows portions of a typical cochlear implant system and the magnetic interaction between the implant magnet and the external holding magnet.
Figure 2:
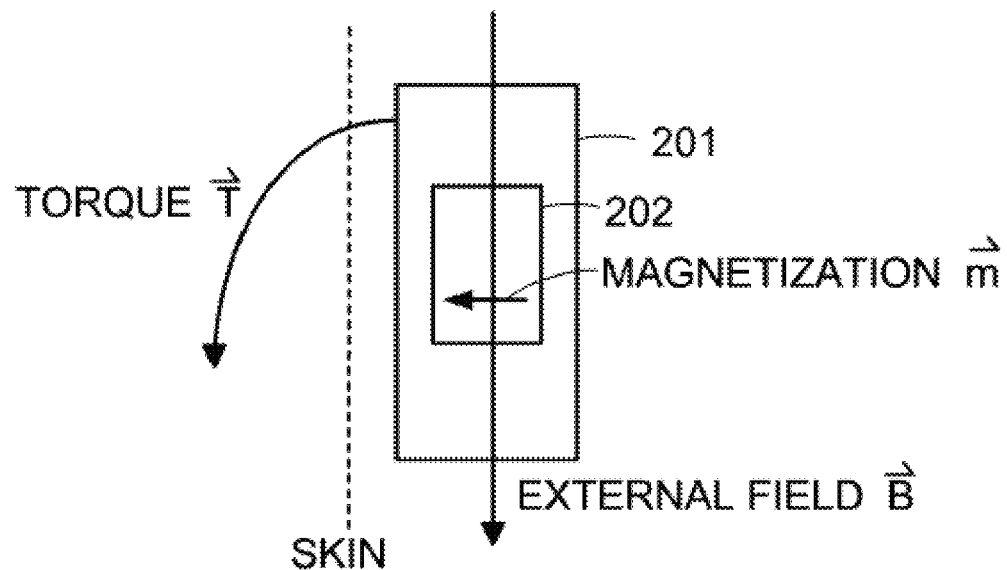
FIG. 2 illustrates the force interactions that can occur between an implant magnet and the applied external magnetic field for an MRI system.
Figure 3:
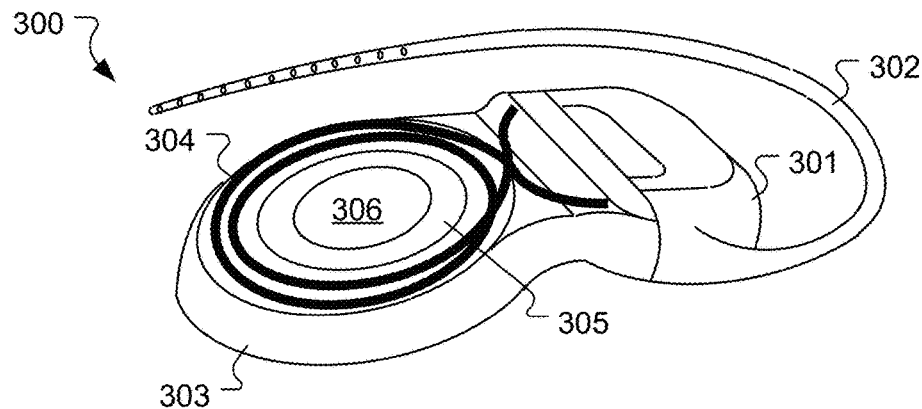
FIG. 3 shows an example of a cochlear implant device with a stiffening ring embedded in the coil case.
Figure 4:
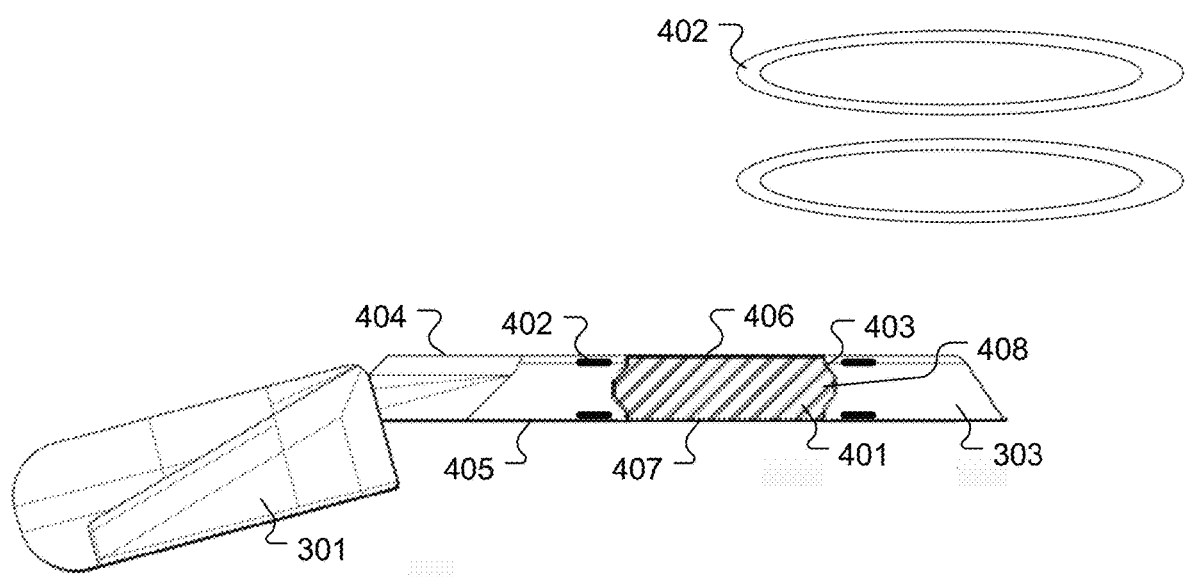
FIG. 4 shows an implant magnet arrangement according to one embodiment of the present invention.

FIG. 4 shows an implant magnet arrangement according to one embodiment of the present invention where an implantable coil case 303 contains a communications coil for transcutaneous communication of an implant communication signal and is made of biocompatible resilient material. A magnet receptacle 403 is located within the coil case 303 and has opposing receptacle openings in the top lateral surface 404 and the bottom medial surface 405 of the coil case 303. An implant magnet 401 fits within the magnet receptacle and has a disc-shape with opposing end surfaces 406 and 407 having corresponding end diameters, and a center body region 408 that is located between the end surfaces 406 and 407 with a corresponding center body diameter larger than the end diameters. The implant magnet 401 and the magnet receptacle 403 are configured to cooperate to permit the implant magnet 401 to be inserted into or removed from the magnet receptacle 403 through either of the receptacle openings in either the top lateral surface 404 and/or the bottom medial surface 405 of the coil case 303.

In further specific embodiments, there may also be at least one stiffening ring 402 embedded in the coil case 303 around the magnet receptacle 403. The at least one stiffening ring 402 resists mechanical torque movement of the coil case 303 and promotes securement of the implant magnet 401 within the magnet receptacle 403. In the specific example shown in FIG. 4, there is a pair of opposing stiffening rings 402 arranged around each of the receptacle openings in the magnet receptacle 403.

The receptacle openings of the magnet receptacle 403 may have a diameter somewhat less than the maximum diameter of the implant magnet 401 (around the center body region 408) to help secure the implant magnet 401 in place within the magnet receptacle 403. To insert or remove the implant magnet 401 into or out of the magnet receptacle, 403, the resilient material of the coil case 303 will allow the receptacle opening to flex a bit wider to allow the implant magnet 401 to pass through. The inner diameter of the stiffening rings 402 should be a bit greater than the maximum diameter of the implant magnet 401 (around the center body region 408); e.g., at least 0.5 mm larger. In some embodiments, the geometry of the stiffening rings 402 may be controlled to interact with one or more surface features on the outer surface of the implant magnet 401 to constitute a facilitate a snap-in mechanism that securely engages the implant magnet 401 within the magnet receptacle 403.

The magnetic field direction of the implant magnet 401 may be like that in a conventional device, perpendicular to the end surfaces 404 and 405. Or the magnetic field direction of the implant magnet 401 may be parallel to the end surfaces 404 and 405, as in the Med-El Synchrony-style device. And the implant magnet 401 and the magnet receptacle 403 may be configured either to allow or to prevent the implant magnet 401 to rotate within the magnet receptacle 403. The side profile of the implant magnet 401 also may have various specific shapes such as shown in FIG. 5 A-C.

The one or more stiffening rings 402 may have various specific structural geometries besides the opposing planar ring arrangement shown in FIG. 4. For example, as shown in FIG. 6 A, a pair of opposing planar stiffening rings 402 may be connected to each other by one or more ring connector elements 601, which provide increased stiffness to the coil case 303. Or, as shown in FIG. 6B, a pair of stiffening rings 402 may have their sides rotated to be perpendicular to the end surfaces 406 and 407 of the implant magnet 401. FIG. 6C shows an embodiment where the stiffening rings 402 have a circular cross-section.

Rather than opposing pairs of stiffening rings, other specific stiffening element structures may be used on some embodiments. For example, FIG. 7 shows an example of a bilevel stiffening ring cage 700 configured to be embedded in the coil case 303 around the magnet receptacle 403. The stiffening ring cage 700 shown has an upper level 701 and a lower level 702 arrangement to cooperate to secure the implant magnet 401 within the magnet receptacle 403. The inner diameter of such a stiffening cage 700 may be somewhat less than the maximum outer diameter of the implant magnet 401 (in the center body region 408). The upper level 701 and a lower level 702 can cooperate to spring outward to expand the inner diameter of the stiffening cage 700 during insertion and removal of the implant magnet 401.

Magnet arrangements such as those shown and discussed present two options for removal and reinsertion of the implant magnet (e.g., for an MRI). The implant magnet can be removed either from underneath on the medial side of the coil case, or from the top lateral side of the coil case. The same two options are available for magnet reinsertion. Due to the symmetric design of the implant magnet and corresponding magnet receptacle, and when the orientation of the magnetic field direction of the disc-shaped magnet is parallel to the end surfaces, a potentially incorrect orientation of the implant magnet is not possible: The magnet can be inserted with either end surface up and there is no wrong "upside-down." In addition, using two or more stiffening rings provides a more secure fixation of the implant magnet within the coil case that is especially robust against rotational forces acting on the implant magnet such as may be occurring during an MRI session.

Any incision required for removal of implant magnets before e.g. undertaking of a MRI-scan shall be as small as possible. For some implant magnet arrangements, surgical removal of the magnet requires a small, but nevertheless always relatively too large incision since the coil case must be lifted up off the underlying bone in order to remove the magnet. Also the surgical tools require sufficient space. But having to move the coil case creates a risk that the entire implant might move and pull out the electrode. In addition, a large semi-circular incision is needed (about 75 mm long) and lifting the coil case can weaken the fibrous capsule that develops which also stabilizes the implant. As an improvement on that, embodiments of the present invention include an implant magnet arrangement with an elastic clamping element that allows removal and reinsertion of the implant magnet via the top lateral side of the implant coil without needing to lift the coil. The elastic clamping element can be easily opened by a slim surgical tool (forceps with angled tips) and the magnet can be fished out (e.g. by a slim ferromagnetic spatula), so the surgical incision may be kept minimal in size.

Figure 8A:
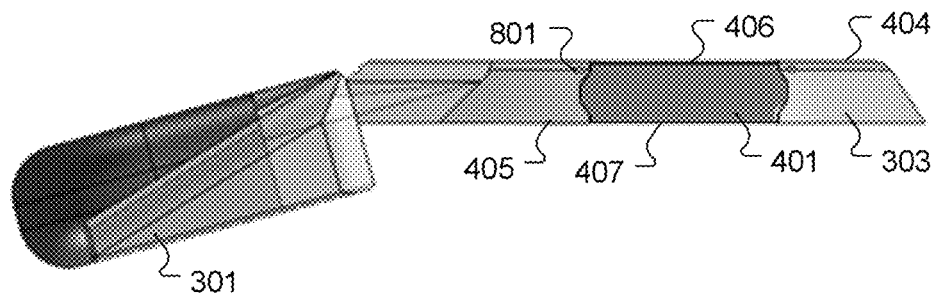
FIG. 8 A-B shows cross-sectional views of an implant magnet with an elastic retainer element according to an embodiment of the present invention.
Figure 8B:
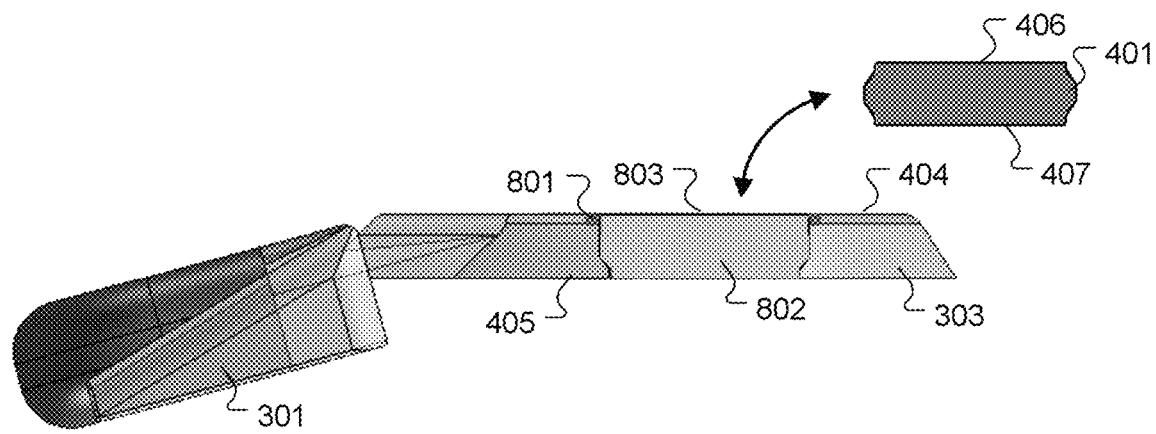

FIGS. 8A-B shows cross-sectional views of an implant magnet 401 with an elastic retainer element 801 according to such an embodiment of the present invention. Implantable coil case 303 contains a communications coil and is made of biocompatible resilient material with a top lateral surface 404. A magnet receptacle 802 is located within the coil case 303 and has a receptacle opening 803 in the top lateral surface 404. An implant magnet 401 fits within the magnet receptacle 802 and has opposing end surfaces, and a center body region located between the end surfaces. The center body diameter is larger than the end diameters. The magnet receptacle 802 has corresponding enclosing surfaces configured to fit against the different diameter surfaces of the implant magnet 401 to secure the implant magnet 401 within the magnet receptacle 802. An elastic retainer element 801, in this case, c-shaped spring ring element, is located radially around the receptacle opening 803 and is configured to normally be closed around the receptacle opening 803 to maintain the implant magnet 401 within the magnet receptacle 802.

The implant magnet 401 and the magnet receptacle 802 may be specifically configured to allow the implant magnet 401 to form fit within the magnet receptacle 802 and hold via friction into place. The friction does not prevent the implant magnet 401 from rotating within the magnet receptacle 802 during e.g. removal or a strong static magnetic field for the MRI. The implant magnet 401 may, for example and without limitation, have a magnetic field direction that is parallel to its end surfaces (in which case the implant magnet can be inserted with either end up), or perpendicular to its end surfaces. It is understood that the invention equally works with implant magnet 401 having any other magnetic field direction.

Figure 9A:
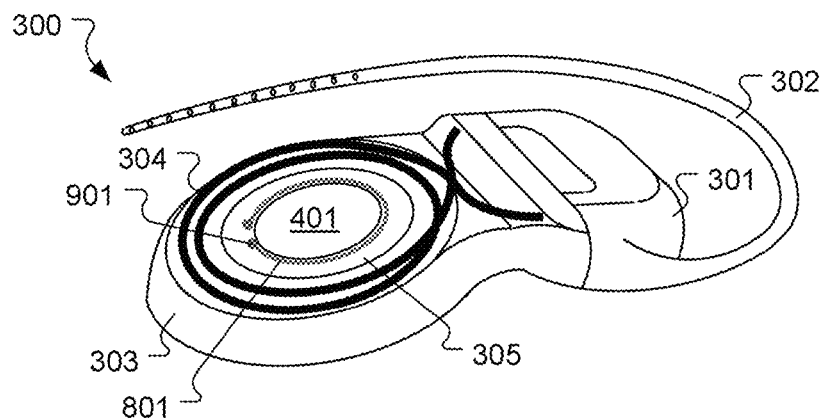
FIG. 9 A-B shows elevated perspective views of an implant magnet with an elastic retainer element according to an embodiment of the present invention.
Figure 9B:
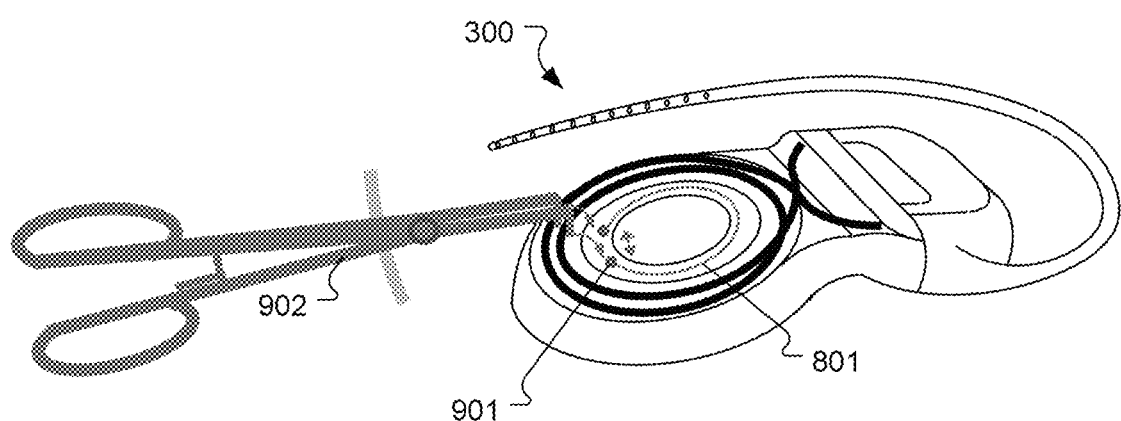

FIG. 9A shows an elevated perspective view of an implant magnet 401 with an elastic retainer element 801 as described above. In one embodiment the retainer element 801 is partially embedded in coil case 303 and only ring end fixtures 901 emerge out from the silicone mold. FIG. 9B shows how the elastic retainer element 801 has ring end fixtures 901 that are configured to cooperate with a surgical handling tool 902 in the form of a forceps with angled ends to expand the receptacle opening 803 to permit the implant magnet 401 to be removed from the magnet receptacle 802 through the receptacle opening 803 without needing to move the coil case 303.

Figure 10A:
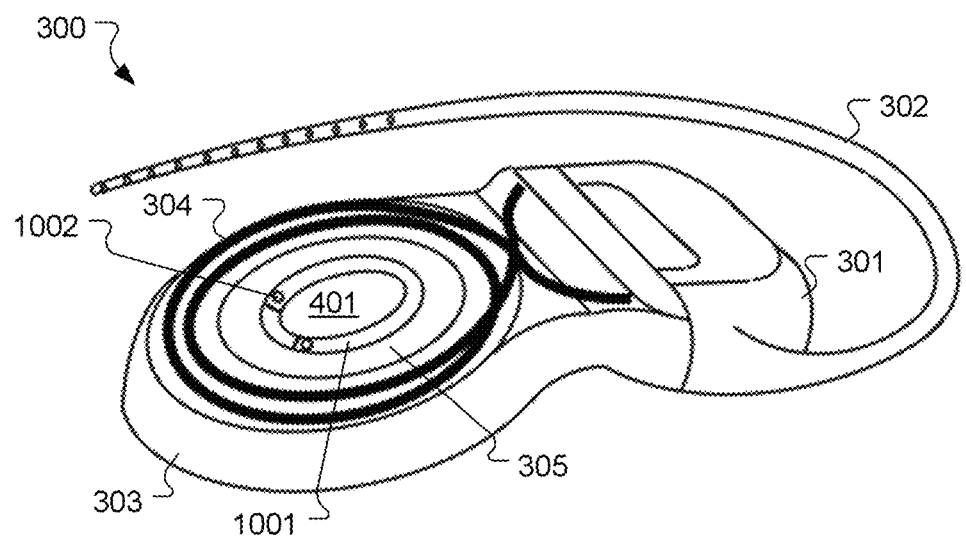
FIG. 10 A-B shows elevated perspective views of an implant magnet with an elastic retainer element according to another embodiment of the present invention.
Figure 10B:
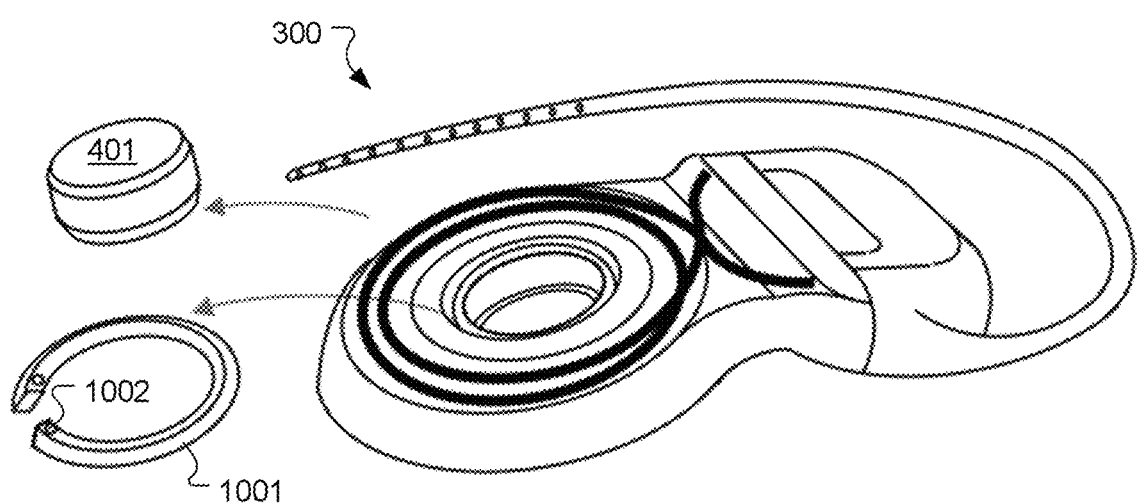
Figure 11A:
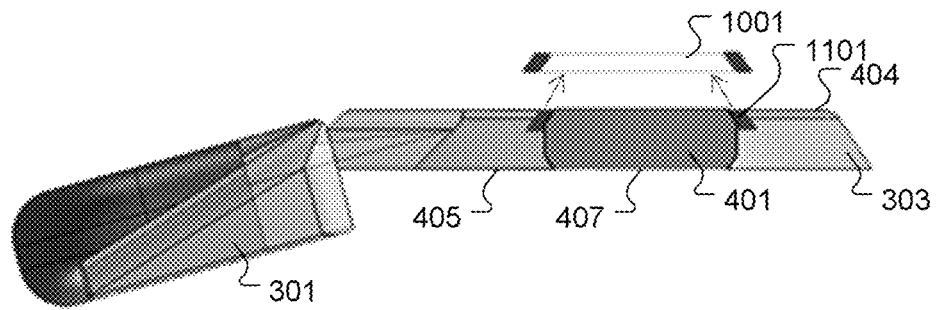
FIG. 11 A-B shows cross-sectional views of an implant magnet with an elastic retainer element according to an embodiment of the present invention.
Figure 11B:
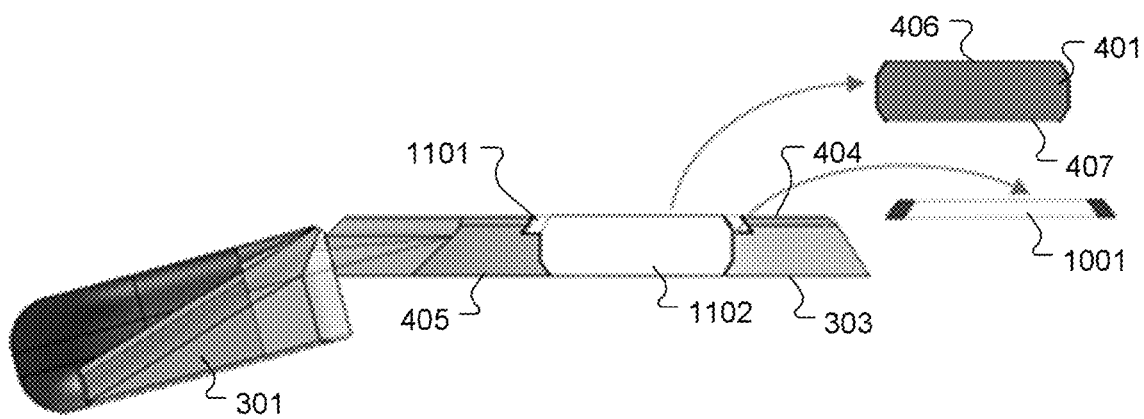

FIGS. 10A-B shows elevated perspective views and FIGS. 11A-B shows cross-sectional views of an implant magnet 401 with another embodiment of removable elastic retainer element 1001 specifically in the form of a c-shaped retainer ring element. Ring end fixtures 1002 are configured to cooperate with a surgical handling tool to allow squeezing and lessen the elastic retainer element 1001 diameter and simultaneously slipping out through the receptacle opening 1101 (as is shown by the arrows in FIG. 11A) and removal of the elastic retainer element 1001. The implant magnet 401 may subsequently be removable via the top lateral surface 404 of the coil case 303 without needing to lift the coil case 303 away from the underlying bone. The smallest inner diameter of receptacle opening 1101 is larger than the widest outer diameter of magnet receptacle 1102. In one embodiment the elastic retainer element 1001 may have parallel side walls, as shown in FIGS. 11A-B, forming a cross-section of parallelogram shape. In a further embodiment elastic retainer element 1001 may have a trapezoidal shaped cross-section with the longer base located at the side having the larger diameter of the elastic retainer element 1001.

FIG. 12 shows an elevated perspective view of an implant magnet 1201 with bayonet elements 1202 according to an embodiment of the present invention. The bayonet elements 1202 engage into slots of the magnet receptacle when the implant magnet 1201 is inserted into the receptacle. The slots may be L-shaped comprising a first channel section perpendicular to the plane of the coil for insertion of the implant magnet 1202 via the top lateral side and a second channel section parallel to the plane of the coil for rotation fixation of the implant magnet 1201 in the magnet receptacle. The second channel section may be adapted for a friction fit of the bayonet elements 1202. In one embodiment the second channel section may be tapering off the first channel section. In addition to or instead, the second channel section may comprise a constriction section for lock engaging the bayonet elements 1202 therein and thereby rotation fixating the implant magnet 1201.

Figure 14A:
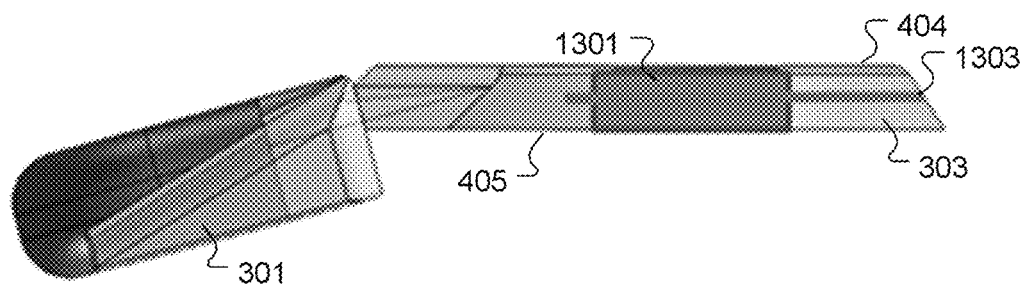
FIG. 14 A-B shows cross-sectional views of an implant magnet with a locking pin according to an embodiment of the present invention.
Figure 14B:
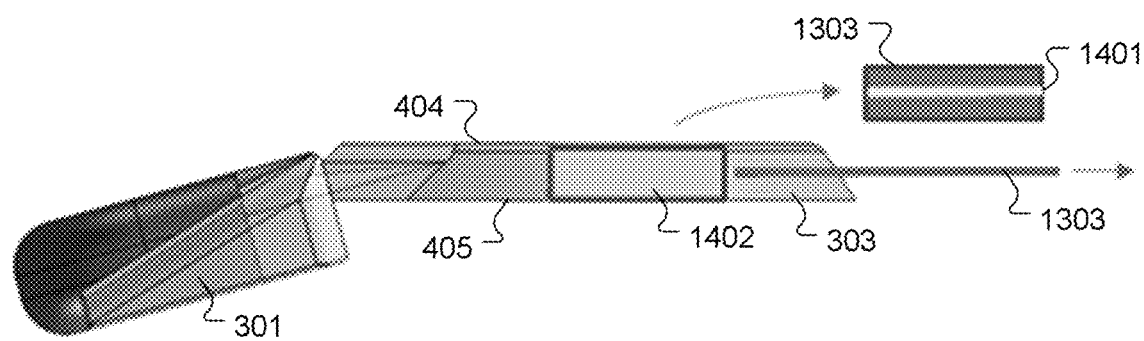

FIG. 13 shows an elevated perspective view and FIG. 14 A-B shows cross-sectional views of an implant magnet 1301 with a locking pin 1303 according to an embodiment of the present invention. The locking pin 1303 may comprise two prongs that are removable through a hole in the coil case 303 parallel to the plane of the coil and perpendicular to the receptacle opening 803. The implant magnet 1301 may comprise two holes 1302 or two notches (not shown) for reception of the prongs of the locking pin 1303. When the locking pin 1303 is inserted into the coil case 303 through the holes, the prongs extend through the coil case 303 and the holes 1302 of the implant magnet 1301 and fixate the same within the coil case 303.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable hearing implant comprising:
    an implantable coil case containing a communications coil for transcutaneous communication of an implant communication signal, the coil case being made of biocompatible resilient material and having a top lateral surface and a bottom medial surface;
    a magnet receptacle located within the coil case;
    opposing receptacle openings in the top lateral surface and the bottom medial surface of the coil case;
    an implant magnet fitting within the magnet receptacle and having:
        i. opposing end surfaces with corresponding end diameters, and
        ii. a center body region located between the end surfaces and having a corresponding center body diameter larger than the end diameters, wherein the implant magnet and the receptacle openings are configured to permit the implant magnet to be inserted into or removed from the implantable hearing implant through the receptacle opening in the top lateral surface and/or the receptacle opening in the bottom medial surface of the coil case; and
    a bilevel stiffening ring cage configured to be embedded in the coil case around the magnet receptacle, the bilevel stiffening ring cage having an upper level and a lower level arrangement that cooperates to secure the implant magnet within the magnet receptacle and that cooperates to expand an inner diameter of the bilevel stiffening ring cage in order to permit the implant magnet to be inserted into or removed from the implantable hearing implant through the receptacle opening in the top lateral surface or the receptacle opening in the bottom medial surface of the coil case.

2. The implantable hearing implant according to claim 1, wherein the inner diameter of the bilevel stiffening ring cage is less than the center body diameter of the implant magnet.

3. The implantable hearing implant according to claim 1, further comprising an elastic retainer element having a ring shape and located radially around the receptacle opening in the top lateral surface or the receptacle opening in the bottom medial surface and that is configured to maintain the implant magnet within the magnet receptacle, wherein the elastic retainer element has opposing ends that include ring end fixtures configured to increase or decrease a diameter of the elastic retainer element, when the ring end fixtures cooperate with a surgical handling tool, in order to permit the implant magnet to be inserted into or removed from the implantable hearing implant through the receptacle opening in the top lateral surface or the receptacle opening in the bottom medial surface of the coil case.

4. The implantable hearing implant according to claim 3, wherein the elastic retainer element is a c-shaped spring ring element.

5. The implantable hearing implant according to claim 3, wherein the elastic retainer element is a c-shaped retainer ring element.

6. The implantable hearing implant according to claim 3, wherein the elastic retainer element is partially embedded in the coil case with the ring end fixtures emerging from the coil case, the ring end fixtures configured to increase the diameter of the elastic retainer element in order to expand the receptacle opening in the top lateral surface or the receptacle opening in the bottom medial surface.

7. The implantable hearing implant according to claim 3, wherein the ring end fixtures are configured to decrease the diameter of the elastic retainer element in order to permit the elastic retainer element to be removed from the receptacle opening in the top lateral surface or the receptacle opening in the bottom medial surface.

8. The implantable hearing implant according to claim 1, wherein the implant magnet has a magnetic dipole having an axis that is parallel to the end surfaces.

9. The implantable hearing implant according to claim 1, wherein the implant magnet has a magnetic dipole having an axis that is perpendicular to the end surfaces.

10. The implantable hearing implant according to claim 1, wherein the implant magnet and the magnet receptacle are configured to allow the implant magnet to rotate within the magnet receptacle.

11. The implantable hearing implant according to claim 1, wherein the implant magnet and the magnet receptacle are configured to prevent the implant magnet from rotating within the magnet receptacle.

12. The implantable hearing implant according to claim 1, wherein the implantable hearing implant is a cochlear implant system.

13. The implantable hearing implant according to claim 1, wherein the implant magnet is disc-shaped.

14. The implantable hearing implant according to claim 13, wherein the implant magnet is cylindrical, elliptical or rectangular with rounded corners.

15. The implantable hearing implant according to claim 1, wherein an outer surface of the implant magnet includes one or more surface features that are configured to interact with the bilevel stiffening ring cage so as to facilitate a snap-in mechanism that securely engages the implant magnet within the magnet receptacle.

16. An implant system comprising:
    the implantable hearing implant according to claim 1; and
    an external device having an external attachment magnet configured to hold the external device in place over the implantable hearing implant on the patient's skin.

17. The implant system according to claim 16, wherein the implantable hearing implant is a cochlear implant.

18. The implant system according to claim 16, wherein the implant magnet is disc-shaped.

19. The implant system according to claim 16, wherein the implant magnet has a magnetic dipole having an axis that is parallel to the end surfaces.

20. The implant system according to claim 16, wherein the implant magnet has a magnetic dipole having an axis that is perpendicular to the end surfaces.

\* \* \* \* \*